United States Patent

Loeffler et al.

Patent Number: 5,095,139
Date of Patent: Mar. 10, 1992

[54] OLIGOPEPTIDE ANTIBIOTICS

[75] Inventors: Wolfgang Loeffler, Basel, Switzerland; Martin Kugler, Wendlingen, Fed. Rep. of Germany; Günther Jung, Tübingen, Fed. Rep. of Germany; Armin Kern, Tübingen, Fed. Rep. of Germany; Claudius Rapp, Tübingen, Fed. Rep. of Germany

[73] Assignee: Ciba-Geigy Corporation, Ardsley, N.Y.

[21] Appl. No.: 514,895

[22] Filed: Apr. 26, 1990

Related U.S. Application Data

[63] Continuation of Ser. No. 103,146, Oct. 1, 1987, abandoned.

[30] Foreign Application Priority Data

Oct. 9, 1986 [DE] Fed. Rep. of Germany ..... 36344370

[51] Int. Cl.$^5$ ............................................... C07F 9/00
[52] U.S. Cl. ...................................................... 562/11
[58] Field of Search ............................................ 562/11

[56] References Cited

FOREIGN PATENT DOCUMENTS 0233154 8/1987 European Pat. Off. .

OTHER PUBLICATIONS

Arch. Biochem., vol. 4, pp. 297-309 (1944).
Arch. Biochem., vol. 22, pp. 208-214 (1949).
The Journal of Antibiotics, vol. 22, No. 10, pp. 467-472 (1969).
Biochem. J., vol. 118, pp. 563-570 (1970).
J. Bacteriology, vol. 51, pp. 363-369 (1946).
Journal of Experimental Pathology, vol. 30, No. 4, pp. 306-319 (1949).
Chmara et al., Biochem. & Biophys. Res. Comm., vol. 52, No. 4, pp. 1381-1387 (1973).
Loeffler et al., J. Phytopathology, vol. 115, pp. 204-213 (1986).
Vanittanakom et al., J. of Antibiotics, vol. 39, pp. 888-901 (1986).
Park et al., Agric. Biol. Chem., vol. 41, pp. 573-579 (1977).
Derwent Abstract of Japanese J53087314 (8/78).
Diddens et al., The Journal of Antibiotics, vol. 32, pp. 87-90.
Agro Bio Chem., 40 (9), 1905-1906 (1976).

*Primary Examiner*—Bruce Gray
*Attorney, Agent, or Firm*—Shawn P. Foley; JoAnn Villamizar

[57] ABSTRACT

Rhizocticines of the formula

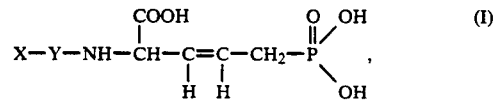

in which X represents hydrogen or a hydrophobic amino acid radical and Y represents a basic amino acid radical, the C2 atoms of the amino acid radicals having the L-configuration, and protected derivatives and salts thereof.

The compounds are obtained from culture broths of *Bacillus subtilis* or synthetically and have especially fungicidal action.

1 Claim, 2 Drawing Sheets

OLIGOPEPTIDE ANTIBIOTICS

This is a continuation of application Ser. No. 103,146 filed on Oct. 1, 1987 now abandoned.

The invention relates to novel di- and tri-peptides, to processes for their manufacture, to extracts and concentrates containing these oligopeptides in enriched form obtained from bacterial culture broths, to the use of the novel peptides as fungicides, nematocides or herbicides, and to pharmaceutical preparations, plant protection agents and herbicidal agents that contain such peptides. The invention relates also to a process for the manufacture of a cleavage product in optically pure form from these peptides and to this optically pure cleavage product itself. The novel di- and tri-peptides are designated rhizocticines A, B, C, D etc., and the cleavage product is L-2-amio-5-phosphone-3-cis-pentoic acid (L-APPA). Rhizocticines have antifungal, nematocidal and herbicidal activities.

The rhizocticines of the present invention can be obtained from bacteria, especially *Bacillus subtilis*. Antifungal extracts from *Bacillus subtilis*, which are designated "Rhizoctonia factor" and "Aspergillus factor", as well as the known antibiotic polypeptide subtilin [Jansen et al., Arch. Biochem. 4, 297 (1944)], are known from H. David Michener et al., Arch. Biochem. 22, 208–214 (1949). The two factors differ in their spectrum of activity, in that unlike the Aspergillus factor the Rhizoctonia factor has virtually no activity against *Aspercillus niger, Aspergillus oryzae,* or *Fusarium lycopersici*. The preparation of the active compounds of these factors in pure form and a clarification of their structure is not known. The pure rhizocticines described herein have an action against *Rhizoctonia solani* that is greater by two powers of ten than that of impure Rhizoctonia factor.

Ebata et al., J. Antibiot. 22, 467–472 (1969) isolated from *Bacillus subtilis* PCI 219, which is identical to ATCC 6633, three antifungal metabolites of the bacillomycin group which they designated subsporins. These antibiotics correspond to the Aspergillus factor in fundamental biological and physical properties, so that there is no doubt as to their identity.

Ebata et al. overlooked the Rhizoctonia factor and bacilysin, a low molecular weight hydrophilic antibiotic similar to the Rhizoctonia factor, which appears earlier.

Bacilysin, the dipeptide N-alanyl-3-(2,3-epoxycyclohexanon-4-yl)-alanine (Walker et al., Biochem. J. 118, 563–565, 1970), was described first in 1946 (Forster et al., J. Bacteriol. 51, 363–369), without details of the chemical structure, under the name bacillin, then in 1949 as bacilysin [Newton, Brit. J. Exptl. Pathol. 30, 306–319 (1949)] and again in 1973 as tetaine [Chmara et al., Biophys. Res. Commun. 52, 1382–1387 (1973)]. In two cases the producers were strains of the *Bacillus subtilis* species and in one instance *Bacillus pumilus*. According to more recent observations [Loeffler et al., J. Phytopathol. 115, 204–213 (1986)], bacilysin has also been formed from *Bacillus subtilis* F-29-3, the fengymycin producer [Vanittanakom et al., J. Antibiot. 39, 888–901 1986)] and from all other tested wild strains of the species *Bacillus subtilis* and from one strain each of the species *Bacillus oumilus* and *Bacillus licheniformis* in various media. The substance inhibits some bacteria and the blastomyces *Saccharomyces cerevisiae* and *Candida albicans,* but unlike the Rhizoctonia factor has virtually no action against hyphal fungi.

Rhizocticine B exhibits a certain similarity to the plumbemycins A and B [Boo Kil. Park et al., Agr. Biol. Chem. 41, 573–579 (1979)] which were, however, isolated from Streptomyces (not particularly closely related to the rhizocticine-producer Bacillus). In addition, the conformity applies only to the L-APPA radical of the tripeptide rhizocticine B, whereas the amino acids adjacent to the L-APPA are different. According to Park et al., the plumbemycins A and B have the formulae L-Ala-L-Asp-D-APPA (A) and L-Ala-L-Asn-D-APPA (B), but the assignment of D to APPA may well be incorrect. The most striking difference lies in the fact that the spectra of activity of rhizocticines on the one hand and of plumbemycins on the other hand are very different and do not overlap. Plumbemycins act only against bacteria, whereas rhizocticines act against fungi.

The invention is based on the isolation, preparation in pure form and structural clarification of rhizocticines A, B, C and D obtained from culture broths of bacteria. Starting from these naturally occurring rhizocticines it is possible to prepare analogous compounds having similar or improved properties in a manner known per se.

The invention relates to rhizocticines of the formula

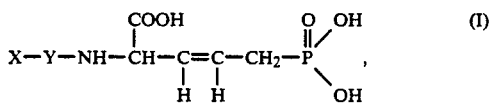

in which X represents hydrogen or a hydrophobic amino acid radical and Y represents a basic amino acid radical, the C2 atoms of the amino acid radicals having the L-configuration, and to protected derivatives and salts thereof.

The abbreviations used are in accordance with the internationally recognized rules of nomenclature. In the abbreviated forms of the peptides, the amino group is to be regarded as being on the left-hand side and the carboxy group on the right-hand side.

Hydrophobic amino acid radicals X are derived from those amino acids which carry a hydrophobic radical at the C2 atom and are especially L-Val, L-Ile, L-Leu or L-Ala. X is preferably hydrogen or L-Val.

Basic amino acid radicals Y are derived from those amino acids which carry a basic radical at the C2 atom and are especially L-Arg, L-Lys, L-Orn or homologs thereof, for example L-HomoArg. Y is preferably L-Arg.

The amino acid on the right-hand side of the formula I has the chemical name L-2-amino-5-phosphono-3-cis-pentenoic acid and is abbreviated to L-APPA.

Preferred rhizocticines of the formula I are those in which X represents hydrogen and Y represents L-Arg (rhizocticine A: L-Arg-L-APPA) or X represents L-Val and Y represents L-Arg (rhizocticine B: L-Val-L-Arg-L-APPA) and their salts.

Other preferred rhizocticines of the formula I are those in which X represents L-Ile and Y represents L-Arg (rhizocticine C: L-Ile-L-Arg-L-APPA) or X represents L-Leu and Y represents L-Arg (rhizocticine D: L-Leu-L-Arg-L-APPA), and their salts.

A further preferred group of rhizocticines of the formula I are L-Val-L-Lys-L-APPA, L-Ala-L-Arg-L-APPA, L-HomoArg-L-APPA, L-Val-L-HomoArg-L-APPA, L-Ile-L-HomoArg-L-APPA, L-Leu-L-HomoArg-L-APPA, L-Ile-L-Lys-L-APPA, L-Leu-L-

Lys-L-APPA, L-Ala-L-Lys-L-APPA, L-Val-L-Orn-L-APPA, L-Ile-L-Orn-L-APPA, L-Leu-L-Orn-L-APPA and L-Ala-L-Orn-L-APPA, and their salts.

Protected derivatives of rhizocticines of the formula I are those in which one or more functional groups are in protected form. Such protecting groups are known in peptide chemistry and can be used in chemical peptide synthesis for protecting the functional groups from undesirable reactions, as described hereinbelow. A special type are protecting groups that can be removed under physiological conditions, which groups can be introduced also after the synthesis and can be removed under physiological conditions, that is to say in vivo.

Salts are especially the internal salts of the rhizocticines of the formula I but may also be acid addition salts or salts with bases. For pharmaceutical purposes there are mainly suitable physiologically tolerable salts, which can also be used, however, for plant protection purposes or as herbicides. Such salts are acid addition salts with inorganic acids, especially mineral acids, for example hydrochloric acid, sulphuric acid or phosphoric acid, or salts with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also amino acids, and methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid.

Rhizocticines having a free phosphono and/or carboxy group can form metal or ammonium salts, such as alkali metal and alkaline earth metal salts, for example sodium, potassium, magnesium or calcium salts, and ammonium salts with ammonia or suitable organic amines, there being especially suitable for the salt formation aliphatic, cycloaliphatic, cycloaliphatic-aliphatic or araliphatic primary, secondary or tertiary mono-, di- or poly-amines, and heterocyclic bases: such as lower alkylamines, for example triethylamine, hydroxy-lower alkylamines, for example 2-hydroxyethylamine, bis-(2-hydroxyethyl)-amine, 2-hydroxyethyldiethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline.

For the purposes of isolation or purification it is also possible to use salts that are pharmaceutically or phytologically unsuitable.

The invention relates also to the processes for the preparation of the rhizocticines of the formula I, their derivatives and salts, characterized in that a) a rhizocticine-producing bacterial strain is cultured in a nutrient medium that may contain an amino acid X or Y or a dipeptide X-Y, and the desired rhizocticine or rhizocticine mixture is isolated from the culture broth, or b) in any sequence, the amino acids X, Y and L-2-amino-5-phosphono-3-cis-pentenoic acid, or protected derivatives thereof, are linked with one another in the manner of a peptide, or c) for the preparation of a rhizocticine of the formula I in which X represents hydrogen, X is removed from a rhizocticine of the formula I in which X represents a hydrophobic amino acid radical, if necessary the protecting group(s) is/are removed, and a resulting rhizocticine of the formula I is converted into a salt or a resulting salt is converted into the free compound.

Process a)

Rhizocticine-producing bacterial strains are especially species of Bacillus, such as, especially, *Bacillus subtilis*, for example ATCC 6633 or F-29-3, or optionally also strains of the Bacillus species mentioned above, such as *Bacillus oumilis* or *Bacillus licheniformis*.

Nutrient media for the production of rhizocticines have an aqueous character and contain carbon and nitrogen sources, mineral salts and defined or complex organic additives. Suitable nutrient media contain, for example, a sugar, such as glucose or mannitol, glycerine, glutamic acid, soya meal, yeast extract, ammonium sulphate, sodium chloride, potassium chloride, potassium hydrogen phosphate, calcium carbonate, magnesium sulphate, iron sulphate, copper sulphate and manganese sulphate, and the like. It is advantageous to use mannitol instead of glucose and additionally an amino acid, especially asparagine or alternatively one of the amino acids or dipeptides that are required for the rhizocticine synthesis and are to be incorporated into the rhizocticines.

The bacterial strain is cultured at from 15° C. to 33° C., preferably at 27° C., in customary fermenters of increasing size under aerobic conditions, preferably until a maximum amount of rhizocticines has been formed.

The working up of the culture broth is effected according to methods known per se, for example after acidification to $pH < 7$, preferably approximately pH 2.5, by means of hydrochloric acid, by separation of the bacterial cells by means of centrifugation or filtration, concentration of the resulting bacteria-free culture broth, for example by evaporation, renewed clarification, for example by centrifugation, concentration to dryness, taking up in ethanol, for example 70% strength ethanol, renewed precipitation by cooling, for example to approximately 4° C., and renewed concentration of the alcoholic supernatant. Concentration is preferably effected by lyophilization. The resulting alcoholic extract contains the rhizocticines in enriched form.

Further purification is effected in an acidic, aqueous phase using adsorber resins, for example Amberlite XAD-16, in a batch process or on a column, and by means of exclusion and ion exchange chromatography, for example on Sephadex CM-15 and Sephadex G-25, it being possible to use deionized water, 5% strength aqueous ethyl alcohol and ammonium acetate buffer pH 4 to pH 5.5 as mobile phases. Rhizocticines A and B can be obtained in pure form by repeated exclusion chromatography, for example on Sephadex G-10 with 15% EtOH/85% $H_2O$ as eluant. High pressure liquid chromatography, for example on RP18 Nucleosil, represents a further purification step.

Rhizocticines C and D can be obtained from the fractions containing prepurified rhizocticine B by high pressure liquid chromatography on RP18 Nucleosil.

For the manufacture of the other rhizocticines falling within the scope of formula I, the corresponding other hydrophobic and basic amino acids, H-X-OH and H-Y-OH, or dipeptides H-X-Y-OH are added to the nutrient medium, and working up is carried out in analogous manner.

The invention relates also to the extracts and concentrates containing the rhizocticines in enriched form obtained from the culture broths.

Process b)

The linking of X, Y and L-APPA to form the desired di- or tri-peptide is effected by the formation of an amide bond between two fragments, namely the carboxy group of the left-hand fragment and the α-amino group of the right-hand fragment. If X is likewise an amino acid, the linking can take place in different sequences, for example by first linking the Y fragment to the L-APPA fragment and linking the reaction product to X, or first linking X to Y and linking the resulting X-Y dipeptide fragment to L-APPA in the manner of an amide.

The methods to be used are generally known in peptide chemistry.

The reaction is preferably carried out as follows: a reactive carboxylic acid derivative of one fragment is reacted with the complementary fragment which has a free α-amino group, it being possible for the activation of the carboxy group of the carboxylic acid derivative also to take place in situ.

Reactive carboxylic acid derivatives are especially reactive activated esters or reactive anhydrides, also reactive cyclic amides; reactive acid derivatives can also be formed in situ.

Activated esters of acids are especially esters unsaturated at the linking carbon atom of the esterifying radical, for example of the vinyl ester type, such as true vinyl esters (which can be obtained, for example, by transesterification of a corresponding ester with vinyl acetate; activated vinyl ester method), carbamoylvinyl esters (which can be obtained, for example, by treatment of the corresponding acid with an isoxazolium reagent; 1,2-oxazolium or Woodward method), or 1-lower alkoxyvinyl esters (which can be obtained, for example, by treatment of the corresponding acid with a lower alkoxyacetylene; ethoxyacetylene method), or esters of the amidino type, such as N,N'-disubstituted amidino esters (which can be obtained, for example, by treatment of the corresponding acid with a suitable N,N'-di-substituted carbodiimide, for example N,N'-dicyclohexylcarbodiimide; carbodiimide method), or N,N-disubstituted amidino esters (which can be obtained, for example, by treatment of the corresponding acid with an N,N-di-substituted cyanamide; cyanamide method), suitable aryl esters, especially phenyl esters suitably substituted by electron-attracting substituents (which can be obtained, for example, by treatment of the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (which can be obtained, for example, by treatment of the corresponding acid with chloracetonitrile in the presence of a base; cyanomethyl esters method), thio esters, especially optionally substituted, for example nitro-substituted, phenylthio esters (which can be obtained, for example, by treatment of the corresponding acid with optionally substituted, for example nitro-substituted, thiophenols, inter alia with the aid of the anhydride or carbodiimide method; activated thiol esters method), amino or amido esters (which can be obtained, for example, by treatment of the corresponding acid with an N-hydroxyamino or N-hydroxyamido compound, for example N-hydroxysuccinimide, N-hydroxypiperidine, N-hydroxyphthalimide or 1-hydroxybenztriazole, for example in accordance with the anhydride or carbodiimide method; activated N-hydroxy esters method), or silyl esters (which can be obtained, for example, by treatment of the corresponding acid with a silylating agent, for example hexamethyldisilazane, and which react readily with hydroxy groups but not with amino groups).

Acid anhydrides may be symmetric or, preferably, mixed anhydrides of these acids, for example anhydrides with inorganic acids, such as acid halides, especially acid chlorides (which can be obtained, for example, by treatment of the corresponding acid with thionyl chloride, phosphorus pentachloride or oxalyl chloride; acid chloride method), azides (which can be obtained, for example, from a corresponding acid ester via the corresponding hydrazide and treatment thereof with nitrous acid; azide method), anhydrides with carbonic acid semiderivatives, such as with corresponding esters, for example carbonic acid lower alkyl semiesters (which can be obtained, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (which can be obtained, for example, by treatment of the corresponding acid with phosphorus oxychloride; phosphorus oxychloride method), or anhydrides with organic acids, such as mixed anhydrides with organic carboxylic acids (which can be obtained, for example, by treatment of the corresponding acid with an optionally substituted lower alkane- or phenylalkane-carboxylic acid halide, for example phenylacetic acid, pivalic acid or trifluoroacetic acid chloride; mixed carboxylic acid anhydrides method), or with organic sulphonic acids (which can be obtained, for example, by treatment of a salt, such as an alkali metal salt, of the corresponding acid with a suitable organic sulphonic acid halide, such as lower alkane- or aryl-, for example methane- or p-toluene-sulphonic acid chloride; mixed sulphonic acid anhydrides method), and symmetric anhydrides (which can be obtained, for example, by condensation of the corresponding acid in the presence of a carbodiimide or 1-diethylaminopropyne; symmetric anhydrides method).

Suitable cyclic amides are especially amides with five-membered diazacycles of aromatic character, such as amides with imidazoles, for example imidazole (which can be obtained, for example, by treatment of the corresponding acid with N,N'-carbonyldiimidazole; imidazolide method), or pyrazoles, for example 3,5-dimethylpyrazole (which can be obtained, for example, via the acid hydrazide by treatment with acetylacetone; pyrazolide method).

As mentioned, the carboxylic acid derivatives may also be formed in situ. Thus, for example, N,N'-di-substituted amidino esters can be formed in situ by reacting a mixture of the complementary fragment having the free amino group and the peptide fragment having the free carboxy group in the presence of a suitable N,N'- disubstituted carbodiimide, for example N,N'-dicyclohexylcarbodiimide. It is also possible to form amino or amido esters of the acid in the presence of the amine to be acylated by reacting a mixture of the corresponding acid and amino starting materials in the presence of an N,N'-disubstituted carbodiimide, for example N,N'-dicyclohexylcarbodiimide, and an N-hydroxyamine or N-hydroxyamide, for example N-hydroxysuccinimide, optionally in the presence of a suitable base, for example 4-dimethylaminopyridine.

Alternatively, process variant b) can be carried out as follows: a fragment having the free carboxy group is reacted with the complementary fragment in which the amino acid is in reactive form. The amino group can be activated, for example, by reaction with a phosphite, for example diethylchlorophosphite, 1,1-phenylenechlorophosphite, ethyldichlorophosphite, ethylenechlorophosphite or tetraethylpyrophosphite.

The amino group can also be activated by being bonded to halocarbonyl, for example chlorocarbonyl, or by being in the form of an isocyanate group.

Free functional groups in the fragments, which, if they are not to participate in the reaction, are therefore advantageously in protected form, are carboxy and amino groups and also the hydroxy groups of L-APPA which, being acidic hydroxy groups, can be protected analogously to the carboxy groups.

Protecting groups and the methods by which they are introduced and removed are described, for example, in "Protective Groups in Organic Chemistry", Plenum Press, London, New York, 1973, and in "Methoden der organischen Chemie", Houben-Weyl, 4th Edition, Vol. 15/1, Georg Thieme Verlag, Stuttgart, 1974, and also in Theodora W. Greene, "Protective Groups in Organic Synthesis", John Wiley & Sons, New York, 1981. It is characteristic of protecting groups that they can be removed readily, that is to say without undesired secondary reactions taking place, for example by solvolysis, reduction, photolysis or alternatively under physiological conditions.

Carboxy groups are customarily protected in esterified form, such ester groupings being readily cleavable under mild conditions. Carboxy groups protected in this manner contain as esterifying groups especially lower alkyl groups branched in the 1-position or suitably substituted in the 1- or 2-position. Preferred carboxy groups in esterified form are inter alia tert.-lower alkoxycarbonyl, for example tert.-butoxycarbonyl, arylmethoxycarbonyl having one or two aryl radicals, these being phenyl radicals optionally mono- or poly-substituted, for example, by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example as mentioned above, for example 4-methoxybenzyloxycarbonyl or 4-nitrobenzyloxycarbonyl, or diphenylmethoxycarbonyl optionally substituted, for example as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group is benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, is an optionally substituted, for example lower alkyl-, lower alkoxy-, aryl-, halo- and/or nitro-substituted, aliphatic, araliphatic, cycloaliphatic or aromatic hydrocarbon radical, such as corresponding, optionally substituted lower alkyl, phenyl-lower alkyl, cycloalkyl or phenyl, for example 2-tri-lower alkylsilylethoxycarbonyl, 2-trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

The organic silyl or stannyl radicals mentioned above and hereinbelow preferably contain lower alkyl, especially methyl, as substituent of the silicon or tin atoms. Corresponding silyl or stannyl groups are especially tri-lower alkylsilyl, especially trimethylsilyl, also dimethyl-tert.-butylsilyl, or correspondingly substituted stannyl, for example tri-n-butylstannyl.

Preferred protected carboxy groups are tert.-lower alkoxycarbonyl, such as tert.-butoxycarbonyl, and especially optionally substituted, for example as mentioned above, benzyloxycarbonyl, such as 4-nitrobenzyloxycarbknyl, or diphenylmethoxycarbonyl, especially 2-(trimethylsilyl)-ethoxycarbonyl.

A protected amino group can be, for example, in the form of a readily cleavable acylamino, arylmethylamino, etherified mercaptoamino, 2-acyl-lower alk-1-enylamino, silylamino or stannylamino group or in the form of an azido group.

In a corresponding acylamino group, acyl is, for example, the acyl radical of an organic carboxylic acid having, for example, up to 18 carbon atoms, especially an alkanecarboxylic acid optionally substituted, for example, by halogen or aryl, or a benzoic acid optionally substituted, for example, by halogen, lower alkoxy or by nitro, or a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl optionally substituted, for example, by halogen, lower alkoxy or by nitro, for example benzoyl, 4-chlorobenzoyl, 4-methoxybenzoyl or 4-nitrobenzoyl, or lower alkoxycarbonyl branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals which are preferably phenyl optionally mono- or poly-substituted, for example, by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, or 9-fluorophenylmethoxycarbonyl, aroylmethoxycarbonyl in which the aroyl group is preferably benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, is an optionally substituted, for example lower alkyl-, lower alkoxy-, aryl-, halo- or nitro-substituted, aliphatic, araliphatic, cycloaliphatic or aromatic hydrocarbon radical having up to 15 carbon atoms, such as corresponding, optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

Other acyl radicals coming into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, optionally substituted, for example nitro-substituted, di-(phenyl-lower alkyl)-phosphoryl, for example dibenzylphosphoryl or di-(4-nitrobenzyl)-phosphoryl, optionally substituted phenoxyphenylphosphonyl, for example phenoxyphenylphosphonyl, di-lower alkylphosphinyl, for example diethylphosphinyl, or optionally substituted diphenylphosphinyl, for example diphenylphosphinyl.

In an arylmethylamino group, which is a mono-, di- or especially tri-arylmethylamino group, the aryl radicals are especially optionally substituted phenyl radicals. Such groups are, for example, benzyl-, diphenylmethyl- and especially trityl-amino.

In a 2-acyl-lower alk-1-en-1-yl radical that can be used as an amino-protecting group, acyl is, for example, the corresponding radical of a lower alkanecarboxylic acid, a benzoic acid optionally substituted, for example, by lower alkyl, such as methyl or tert.-butyl, lower alkoxy, such as methoxy, halogen, such as chlorine, and/or by nitro, or especially a carbonic acid semiester, such as a carbonic acid lower alkyl semiester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

An amino group can also be protected in protonated form; as corresponding anions there come into consideration especially those of strong inorganic acids, such as hydrohalic acids, for example the chlorine or bromine anion, or organic sulphonic acids, such as p-toluenesulphonic acid.

Preferred amino-protecting groups are acyl radicals of carbonic acid semiesters, especially tert.-butoxycarbonyl, or optionally substituted, for example as indicated, benzyloxycarbonyl (BOC), for example 4-nitrobenzyloxycarbonyl, or diphenylmethoxycarbonyl, or 9-fluorenylmethoxycarbonyl (Fmoc), or 2-halo-lower alkoxycarbonyl, such as 2,2,2-trichloroethoxycarbonyl, and also trityl or formyl.

A protecting group, such as, especially, a carboxy-protecting group, in the sense of this application is to be understood as being also a polymeric carrier bonded in a readily removable manner to the functional group, such as, especially, a carboxy group, to be protected, as is suitable, for example, for the Merrifield synthesis. Such a suitable polymeric carrier is, for example, a polystyrene resin weakly cross-linked to divinylbenzene by copolymerization, which carries bridge members suitable for reversible bonding of the peptide radicals.

The reaction can be carried out in a manner known per se, the reaction conditions depending especially upon whether and, if so, how the carboxy group participating in the reaction has been activated, customarily in the presence of a suitable solvent or diluent or a mixture thereof, and, if necessary, in the presence of a condensation agent which may also be an acid-binding agent if, for example, the carboxy group participating in the reaction is in anhydride form, while cooling or heating, for example in a temperature range of from approximately $-30°$ C. to approximately $+150°$ C., in a closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulphonate and 2-tert.-butyl-5-methyl-isoxazolium perchlorate, or a suitable acylamino compound, for example 2-ethoxy-1-ethoxycarbonyl-1,2-dihydroquinoline., Customary acid-binding condensation agents are, for example, alkali metal carbonates or hydrogen carbonates, for example sodium or potassium carbonate or hydrogen carbonate (customarily together with a sulphate), or organic bases, such as customarily sterically hindered tri-lower alkylamines, for example N,N-diisopropyl-N-ethylamine.

Process c)

Customary amide cleavage methods may be used to remove the hydrophobic amino acid radical X from a rhizocticine of the formula X-Y-L-APPA. The cleavage can be carried out in an acidic medium, for example with hydrochloric acid, extensive hydrolysis of the desired cleavage products of the formula Y-L-APPA being avoided by suitable adjustment of the pH value, temperature and duration.

X is preferably removed enzymatically by means of a protease, for example thermolysin or especially pronase, for example obtained from *Streptomyces griseus.*

The removal of the protecting groups is effected in a manner known per se, for example by means of solvolysis, especially hydrolysis, alcoholysis or acidolysis, or by means of reduction, especially hydrogenolysis or chemical reduction, optionally in stages or simultaneously, it also being possible to use enzymatic methods.

For example, tert.-lower alkoxycarbonyl, or lower alkoxycarbonyl substituted in the 2-position by an organic silyl group or in the 1-position by lower alkoxy or by lower alkylthio, or optionally substituted diphenylmethoxycarbonyl can be converted into free carboxy, for example by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst Suitably substituted benzyloxycarbonyl, such as 4-nitrobenzyloxycarbonyl, can be converted into free carboxy also by means of chemical reduction, for example by treatment with an alkali metal dithionite, for example sodium dithionite, or with a reducing metal, for example zinc, or reducing metal salt, such as a chromium(II) salt, for example chromium(II) chloride, customarily in the presence of a hydrogen-yielding agent which together with the metal is capable of producing nascent hydrogen, such as an acid, especially a suitable carboxylic acid, such as an optionally substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or of an alcohol or thiol, it being preferable to add water. By treatment with a reducing metal or metal salt, as described above, it is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl likewise by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid that yields the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide.

A protected amino group is freed in a manner known per se and, depending upon the nature of the protecting groups, in various ways, preferably by solvolysis or reduction. 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino can be cleaved also by treatment with an alkali metal dithionite, for example sodium dithionite. Optionally substituted diphenylmethoxycarbonylamino, tert.-lower alkoxycarbonylamino or 2-trisubstituted silylethoxycarbonylamino can be cleaved by treatment with a suitable acid, for example formic or trifluoroacetic acid, optionally substituted benzyloxycarbonylamino can be cleaved, for example, by means of hydrogenolysis, that is to say by treatment with hydrogen in the presence of a suitable hydrogenation catalyst, such as a palladium catalyst, optionally substituted triarylmethylamino or formylamino can be cleaved, for example, by treatment with an acid, such as a mineral acid, for example hydrochloric acid, or an organic acid, for example formic, acetic or trifluoroacetic acid, optionally in the presence of water, and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and subsequent solvolysis, such as alcoholysis or hydrolysis, of the resulting condensation product. A 9-fluorenylmethoxycarbonyl group can be removed by means of a base, especially piperidine or piperazine. An amino group protected by 2-substituted silylethoxycarbonyl can be converted into the free amino group also by treatment with a salt of hydrofluoric acid that yields fluoride anions, as indicated above in connection with the freeing of a correspondingly protected carboxy group.

Amino protected in the form of an azido group is converted into free amino, for example, by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or while cooling or heating.

If several protected functional groups are present, if desired the protecting groups are so chosen that more than one such group can be removed at the same time, for example by acidolysis, such as by treatment with trifluoroacetic acid or formic acid, or by reduction, such as by treatment with zinc and acetic acid, or with hydrogen and a hydrogenation catalyst, such as a palladium-on-carbon catalyst.

Salts of rhizocticines are prepared according to customary methods, for example by reaction with the corresponding acid or base in a suitable solvent, such as water or ethanol, and evaporation of the solvent, or in a non-polar solvent, such as ether or tetrahydrofuran and/or pentane, and precipitation of the salt. For the preparation of the salts and the free compounds that are present in the form of internal salts, it is also possible to use ion exchange resins in a manner known per se.

The rhizocticines of the present invention have fungicidal, nematocidal and herbicidal activities, as can be demonstrated in the following tests. For the tests for biological characterization, a rhizocticine preparation having a specific activity of approximately 35% was used.

Activity against nematodes

In a test against *Caenorhabditis eleoans* the rhizocticines have a lethal action against all nematodes in concentrations of down to 10 µg/ml within two days. In the case of rhizocticine concentrations of 3.5 µg/ml the movement of the nematodes is reduced in comparison with the control.

Herbicidal activity

At 70 µg/ml the root growth of *Leoidium sativum* is slightly reduced.

Spectrum of microorganisms inhibited by rhizocticines

Profiles of activity: fungi (Table 1); prokaryotes (Table 2).

The inhibiting areola diameters were determined for all the given concentrations. The effective concentrations are given in the lines from left to right (in each case as mm inhibiting areola diameter) and where there are no figures given on the right-hand side the empty positions indicate "no action", exception: *Microsporum ovoseum* (under "Onygenales.,.") where the diffusion test could not be evaluated (activity was shown, however, using a different test procedure).

MIC, IC50 and IC10 values for thread fungi were determined as follows: Rhizocticine solutions in 35% ethanol were prepared in various concentrations. 50 µl solutions were introduced into 5 ml of sterile malt agar at 45° C. and poured into sterile Petri dishes (55 mm diameter). The concentrations of rhizocticine were 3.5, 1.1, 0.35, 0.11, 0.035 and 0.011 μg/ml. The plates were inoculated centrally with cylindrical pieces of agar (6 mm diameter) from the peripheral zone of growing fungal colonies. Over a period of from two to ten days the diameter of the growing colonies was measured. The resulting data were used for determining the minimum inhibiting concentrations (MIC) and the concentrations at which the antibiotic brings about a 50% (IC50) and a 10% (IC10) inhibition of growth. Control plates without antibiotic were used as a reference (100% growth).

The minimum inhibiting concentrations for blastomyces (MIC) were determined in microtitre plates (24 depressions, 16 mm diameter; Costar, Cambridge, USA). These contained, per depression, 940 μl of malt medium, 50 μl of a preculture cultured overnight in malt medium, and 10 μl of a rhizocticine solution in 35% strength ethanol. The final rhizocticine concentrations were in the region of from 3.5 to 0.011 μg/ml. After an incubation period of 24 hours, those concentrations in the dilution series at which no growth of the germs could be detected were designated MIC.

In the Table, lines without figures in the corresponding columns indicate that no tests (MIC, IC50, IC10) have been carried out.

TABLE 1

| | Antifungal activity of the rhizocticine against fungi (malt medium) | | | | | | | | |
|---|---|---|---|---|---|---|---|---|---|
| | Inhibiting areola diameter (mm) per roundel of applied amount (ng) | | | | | | Inhibiting | | |
| FUNGI | $3.5 \times 10^3$ | $1.1 \times 10^3$ | $3.5 \times 10^2$ | $1.1 \times 10^2$ | $3.5 \times 10^1$ | $1.1 \times 10^1$ | areola type | MIC | IC50 (μg/ml) |
| ZYGOMYCOTA | | | | | | | | | |
| *Basidiobolus microsporus* | 48 | 39 | 34 | | | | n | | |
| *Entomophthora coronata* | 35 | | | | | | W+ | | |
| *Mycotypha africana* | 22 | 17.5 | 13 | 10 | | | W | | |
| *Rhizomucor miehei* | 32 | 27 | 23 | 21 | | | W | >3.5 | >3.5 |
| ASCOMYCOTA AND DEUTEROMYCOTA | | | | | | | | | |
| Endomycetes and associated Blastomycetes | | | | | | | | | |
| *Candida albicans* | 21 | 19 | 13 | | | | W | ~3.5 | |
| *Candida guilliermondii* | 19 | 14 | + | | | | n | >3.5 | |
| *Dipodascus magnusii* | 32 | 26 | 14 | | | | n | >3.5 | |
| *Nematospora coryli* | 49 | 40 | 31 | | | | W+ | >3.5 | |
| *Saccharomyces cerevisiea* | 25 | 21.5 | 17 | 12.5 | | | n | ~0.35 | |
| *Saccharomycopsis lipolytica* | 37 | 33.5 | 28 | 23 | 17 | + | n | 0.35 | |
| *Schizosaccharomyces pombe* | 54 | 48 | 23.5 | 23.5 | + | | n | 0.35 | |
| Eurotiales and associated Deuteromycota | | | | | | | | | |
| *Aspergillus fumigatus* | 29 | 24 | 19 | + | | | W | | |
| *Aspergillus terreus* | 20 | | | | | | W | | |
| *Paecilomyces variotii* | 46 | 41 | 34 | 31 | 20 | 14 | n | >3.5 | 1.1 |
| *Penicillium notatum* | 36 | 26 | 20 | + | | | W | | |
| Onygenales and associated Deuteromycota | | | | | | | | | |
| *Epidermomyces floccosus* | + | | | | | | W+ | | |
| *Microsporum gypseum* | | | | | | | | >3.5 | >3.5 |
| *Trichophyton erinacei* | 44 | 37 | 23 | | | | W | >3.5 | >3.5 |
| *Trichophyton mentagrophytes* | 39 | 27 | 17 | | | | W+ | | |
| *Trichophyton rubrum* | 44 | 28 | 15 | | | | W | >3.5 | >3.5 |
| Sphaeriales and associated Deuteromycota | | | | | | | | | |
| Fusarium sp. TO 8014 | 17.5 | 14 | 11 | | | | n | | |
| *Sordaria macrospora* | 35 | 20 | + | | | | n | | |
| Pezizales | | | | | | | | | |
| *Ascobolus carbonarius* | 28 | | | | | | * | | |
| *Ascodesmis sphaerospora* | 52 | 47 | 39 | 33 | 19 | | n | 3.5 | 0.35 |
| *Plicaria anthracina* | 37 | 25 | 25 | | | | * | 3.5 | 0.35 |
| Dothideales and associated Deuteromycota | | | | | | | | | |
| *Alternaria kikuchiana* | 38 | 30 | 19 | + | | | W | | |
| *Cladosporium carrionii* No. 1 | 17 | | | | | | W+ | | |
| *Cladosporium trichoides* No. 3.4 | — | | | | | | | | |
| *Curvularia lunata* | 28 | 18 | 14 | | | | W | | |
| *Stemphylium sarciniforme* | 44 | 37 | 29 | 20 | | | W | | |
| Stemphylium sp. TO 609 | 42 | 34 | 27 | 24 | | | n | | |
| Dematiaceae (blackening fungi) of uncertain classification | | | | | | | | | |
| *Exophiala mansonii* No. 5, 6, 10 | — | | | | | | W+ | | |
| *Exophiala werneckii* | 16 | | | | | | W+ | | |
| *Rhinocladiella compacta* | 16 | | | | | | W+ | | |
| *Rhinocladiella pedrosoi* | 16 | | | | | | W+ | | |
| BASIDIOMYCOTA AND ASSOCIATED DEUTEROMYCOTA | | | | | | | | | |
| *Rhizoctonia solani* | — | | | | | | * | ~3.5 | 0.35 |
| *Rhodotorula rubra* | + | | | | | | W+ | >3.5 | |

TABLE 1-continued

| | Antifungal activity of the rhizocticine against fungi (malt medium) | | | | | | | | |
|---|---|---|---|---|---|---|---|---|---|
| | Inhibiting areola diameter (mm) per roundel of applied amount (ng) | | | | | | Inhibiting | | |
| FUNGI | $3.5 \times 10^3$ | $1.1 \times 10^3$ | $3.5 \times 10^2$ | $1.1 \times 10^2$ | $3.5 \times 10^1$ | $1.1 \times 10^1$ | areola type | MIC | IC50 (µg/ml) |
| *Ustilago maydis* | — | | | | | | | | >3.5 |

Appendix to Table 1:
IC10 corresponds to 10% inhibition of growth
IC50 corresponds to 50% inhibition of growth
MIC minimum inhibiting concentration
inhibiting areola type:
n very weak growth
W weak to moderate growth
W+ strong growth
*test on giant colony

TABLE 2

| Rhizocticine-insensitive prokaryotes (no inhibition when tested against 3.5 µg of rhizocticine per roundel) | |
|---|---|
| | medium, temperature (°C.) |
| GRAM-POSITIVE BACTERIA | |
| *Arthrobacter aurescens* | NB, 27 |
| *Arthrobacter oxydans* | NB, 27 |
| *Bacillus cereus* | nHA, 37 |
| *Bacillus subtilis* | Ox, MB, 37 |
| *Brevibacterium flavum* | Ox, 37 |
| *Clostridium pasteurianum* | Clost, 27 |
| *Corynebacterium insidiosum* | Ox, 27 |
| *Micrococcus luteus* | NB, 27 |
| *Staphylococcus aureus* | Ox, 37 |
| *Streptomyces glaucescens* | nHA, 27 |
| *Streptomyces violaceoruber* | nHA, 27 |
| *Streptomyces viridochromogenes* | nHA, 27 |
| GRAM-NEGATIVE BACTERIA | |
| *Achromobacter geminiani* | nHA, 37 |
| *Escherichia coli* | Ox, MB, 37 |
| *Proteus mirabilis* | NB, 37 |
| *Proteus vulgaris* | NB, 37 |
| *Pseudomonas fluorescens* | NB, 27 |
| *Salmonella typhimurium* | nHA, 37 |

TEST MEDIA

The figures given for the test media relate to 1 liter of deionized water.

NB medium: Nutrient Broth 8.0 g, pH 7.0 nHA medium: Yeast extract 4.0 g, malt extract 10.0 g, glucose 4.0 g, pH 7.3

Ox medium: Ox Lba Lemco meat extract 10.0 g, peptone obtained from casein 10.0 g, NaCl 5.0 g, pH 7.2

MB medium glucose 8.0 g, NaCl 5.0 g, diammonium tartrate 4.0 g, $MgSO_4 \times 7H_2O$ 1.0 g, $K_2HPO_4$ 2.0 g, $CaCl_2$ 200 mg, $MnSO_2 \times H_2O$ 10 mg, ferrioxamine B 20.0 mg, pH 7.0

Closet medium: peptone obtained from casein 20.0 g, glucose 5.0 g, malt extract 3.0 g, Ox Lab Lemco meat extract 3 0 g, yeast extract 3.0 g, ascorbic acid 200.0 mg, pH 7.0

MA medium: malt extract 20.0 g, pH measured 6.0

For solid nutrient media, 20 g/l of Difco agar were added.

The invention relates also to the use of rhizocticines of the formula I and their salts, and of extracts or concentrates containing rhizocticines, as fungicides, nematocides or herbicides.

The invention relates also to pharmaceutical preparations that contain as active ingredient an effective dose of one of the rhizocticines according to the invention or a salt thereof together with a significant amount of a pharmaceutical carrier, especially preparations for oral, parenteral, such as intramuscular or intravenous, or topical administration to warm-blooded animals, such as, more especially, humans.

The dosage of the active ingredient depends upon the species of warm-blooded animal, body weight, age and individual condition, the disease to be treated and upon the method of administration. The dose for a warm-blooded animal weighing approximately 70 kg is generally approximately from 50 to 500 mg. The pharmaceutical preparations according to the invention are suitable for oral or parenteral, for example i.v. or i.m., or topical administration.

The pharmaceutical preparations according to the invention are suitable for oral or parenteral, for example i.v. or i.m., or especially for topical administration.

For example, the active ingredients of the formula I of the present invention are used in the form of injectable, for example intravenously administrable preparations or infusion solutions. Such solutions are preferably isotonic aqueous solutions or suspensions which can be prepared before use, for example from lyophilized preparations which contain the pure active ingredient or the active ingredient together with a carrier, for example mannitol Pharmaceutical preparations for oral use may be sterilized and may contain adjuncts, for example preservatives, stabilizers, wetting agents and/or emulsifiers, solubilizers, salts for regulating the osmotic pressure and/or buffers. For topical use there are especially suitable sprays, lotions and powders, also pessaries, for example vaginal pessaries, which are manufactured in customary manner. The present pharmaceutical preparations which, if desired, may contain further pharmacologically valuable substances, for example further active ingredients, contain approximately from 0.1% to 100%, especially approximately from 1% to 100%, active ingredient.

The pharmaceutical preparations are manufactured in a manner known per se, for example by means of conventional processes described in pharmacopoeiae.

The pharmaceutical preparations of the present invention can be used in a method for the therapeutic treatment of the human or animal body, for example for the treatment of infections that are caused by fungi or nematodes.

Further scope for the use of the rhizocticines of the formula I and their salts lies in the field of plant protection, for example in the control of fungal diseases in plants, for example in greenhouse crops, in the treatment of infected trees etc., For this use there are suitable, for example, aerosols. It is also possible to use for this purpose crude extracts and concentrates obtained from rhizocticine-producing bacterial strains.

The invention therefore relates also to plant protection agents containing a rhizocticine of the formula I or a salt thereof tolerable by plants or rhizocticine-containing extracts or concentrates obtained from rhizocticine-producing bacterial strains, especially from *Bacillus subtilis* ATCC 6633.

The plant protection agents contain a fungicidally effective amount of rhizocticines in pulverulent or dissolved form. Application is preferably effected in sprayable aqueous solution.

The invention relates also to the use of the rhizocticines as herbicidal agents. Such herbicidal agents contain a rhizocticine of the formula I or a salt thereof or rhizocticine-containing extracts or concentrates obtained from rhizocticine-producing bacterial strains, especially from *Bacillus subtilis* ATCC 6633.

The invention relates also to a process for the preparation of optically pure L-2-amino-5-phosphono-3-cis-pentenoic acid (L-APPA), characterised in that a rhizocticine or mixture of rhizocticines obtained by fermentation of a rhizocticine-producing bacterial strain is cleaved by hydrolysis and the L-APPA is isolated in optically pure form.

The rhizocticines prepared as described hereinbefore, especially rhizocticine A, B, C or D, or mixtures thereof, are separated into the individual amino acids by hydrolysis in a manner known per se. The hydrolytic cleavage can be carried out under acidic conditions, for example with 6N hydrochloric acid at temperatures of up to approximately 110° C., or preferably enzymatically, for example by treatment with a protease, for example thermolysin, carboxypeptidase A or trypsin, at temperatures of from room temperature to 45° C., and preferably, depending upon the enzyme, at approximately from 29° C. to 41° C.

The isolation of L-APPA is effected by chromatography, for example by means of ion exchangers, such as Dowex 50 WX8, or one of the purification methods customary in peptide chemistry.

The invention relates also to the optically pure L-2-amino-5-phosphono-3-cis-pentenoic acid and salts thereof.

Salts of L-APPA are those with the same acids and bases as those mentioned under the rhizocticine salts.

EXAMPLES

The following culture media are used in the Examples.

| Complex production medium (T medium) | |
|---|---|
| glucose | 15.0 g |
| glycerine | 10.0 g |
| soya meal | 15.0 g |
| (NH4)SO4 | 5.0 g |
| yeast extract | 1.0 g |
| NaCl | 5.0 g |
| CaCO3 | 5.0 g |
| deionised water | 1 l |
| pH | 7.3 |
| Defined production medium (PL medium) | |
| mannitol | 20.0 g |
| asparagine | 1.0 g |
| glutamic acid | 5.0 g |
| KHPO4 | 1.0 g |
| MgSO4 × 7 H2O | 500.0 mg |
| KCl | 500.0 mg |
| FeSO3 × 7 H2O | 0.15 mg |
| CuSO3 × 5 H2O | 0.16 mg |

| -continued | |
|---|---|
| MnSO4 | 5.0 mg |
| deionised water | 1 l |
| pH | 6.0 |

The microorganism *Bacillus subtilis* used in the Examples is known and is available commercially, for example under the reference number ATCC 6633 from the American Type Culture Collection.

The same strain can also be obtained from the following depositories (depository/reference): National Collection of Industrial Bacteria/NCIB 8054, Institute for Fermentation/IFO 13720, National Collection of Type Cultures/NCTC 10400, Institute of Applied Microbiology/IAM 1069, Deutsche Sammlung von Mikroorganismen/DSM 347.

The strain used, ATCC 6633, was deposited again with the Deutsche Sammlung von Mikroorganismen, Grisebachstr. 8, D-3400 Göttingen on 2nd February, 1987, in accordance with the Budapest Treaty and was given the deposit number DMS 3973 (depositor's reference BS6633).

The following abbreviations are used:
AA:amino acid
Boc:tert.-butoxycarbonyl
TLC:thin-layer chromatography
DCC:dicyclohexylcarbodiimide
DCU:dicyclohexylurea
DMF:dimethylformamide
Fmoc:9-fluorenylmethoxycarbonyl
GC:gas chromatography
HOBt:hydroxybenzotriazole
OSu:N-hydroxysuccinimide ester
TFA:trifluoroacetic acid

EXAMPLE 1

Fermentation on a flask scale 500 flasks having a lateral insert (baffle) and containing 100 ml of nutrient solution (PL medium) are each inoculated with 0.4 ml of spore suspension of ATCC 6633 and incubated on a rotary shaking machine at 120 rpm and 27° C. for approximately 72 hours.

EXAMPLE 2

Fermentation on a 20 l scale

Fermentation is carried out in a bioreactor with an instrument unit for measuring and regulating the propeller speed, the temperature, the pH, the ventilation and the addition of anti-foam agent. An Intensor tumble system ensures that the nutrient solution circulates in the stirring vessel. The reactor is filled with 19 l of nutrient solution (PL) and sterilized in situ (20 min. at 121° C. and 1 atm excess pressure). After cooling, the solution is inoculated with 5% of an at least 10-day old well-spored culture (see Example 1) and incubated at 27° C., 800 rpm and 5 1/min. air throughput. In order to suppress the formation of foam anti-foam agent is metered in as required.

Harvest is effected after approximately 60 hours, when the production maximum has been reached, by centrifuging off the cellular substance. FIG. 1 shows a fermentation on the 20 l scale.

EXAMPLE 3

Fermentation on a 200 l scale

Production of the desired compounds is carried out in a bioreactor with an instrument unit for measuring and regulating the propeller speed, the temperature, the pH, the ventilation and the addition of anti-foam agent using a foam probe. Ventilation is effected under the surface in an Intensor tumble system. Serialization is effected in situ using 200 l of nutrient solution (PL) in accordance with an in-house program. The inoculating material, 5 l of an at least 10-day old preculture described in Example 1, is pumped in directly by way of a hose line. Fermentation parameters: 27° C., 800 rpm (propeller speed) and 50 l/min. air throughput.

Harvest is effected after approximately 60-80 hours, when a maximum concentration of the desired compounds has been reached.

After harvesting the compounds can be isolated from the culture filtrate using customary chemical/physical methods, which are predominantly chromatographic and spectroscopic methods.

Yield of the rhizocticines in relation to the culture filtrate: approximately 30 mg/l, that is to say 60 g per fermenter.

FIG. 2 shows fermentation on the 200 l scale.

EXAMPLE 4

Working-up from a PL medium on a 5 l scale using Amberlite XAD-16 (batch process) and Sephadex CM-25 and G-15

5 l of culture broth are adjusted to pH 2.5 with 5N HCl. The resulting precipitate is separated off in a Sorvall centrifuge having a GSC 3 rotor at 10,000 g (approximately 8,000 rpm) and discarded. The supernatant (4.5 l) is then concentrated to dryness at 50° C. and taken up in 500 ml of 70% ethanol.

Precipitation is carried out again at 4° C. and the precipitate is separated from the highly active supernatant. The precipitate is extracted twice with 200 ml of 70% ethanol each time and the active supernatants are combined and concentrated.

The brownish concentrate is then taken up in 500 ml of deionized water, the pH is adjusted to 3 and the whole is stirred for one hour in a batch process with 150 g of Amberlite XAD-16 As a result, melanin-like and lipophilic impurities can become bonded to the adsorber resin, whereas the rhizocticines are not adsorbed. The adsorber resin is separated off and washed with 200 ml of deionized water and the aqueous fractions are combined. The purification process with Amberlite XAD-16 is repeated and the entire aqueous volume is concentrated.

The lyophilisate is taken up in 10-15 ml of 5% ethanol and purified further by gel filtration over Sephadex G-15 with 5% ethanol. The active fractions are combined, lyophilized and taken up in 2 ml of 5% ethanol. A second chromatography run is then carried out using a second G-15 column.

The lyophilized, active fractions from the preceding step are dissolved in 2 ml of 5 mM ammonium acetate buffer pH 4 and introduced onto a Sephadex CM-25 column. While most impurities do not bind to the weak ion exchanger in the case of the above-mentioned buffer, the rhizocticines are retained During the elution with 100 mM ammonium acetate buffer pH 4, the rhizocticines A and B (described earlier as rhizocticines I and III, respectively) can be separated from one another.

The final purification of the rhizocticines is effected by means of exclusion chromatography on Sephadex G-15.

EXAMPLE 5

Working-up from PL medium on a 25 l and 200 l scale using an Amberlite XAD-16 column and Sephadex CH-25 and G-15

During the working-up of 25 and 200 l fermenters, the cellular substance is adjusted to a pH of from 2.5 to 3 and separated off in a sludge centrifuge. Concentrating immediately in a thin-layer evaporator or by similar methods is not possible, or can be carried out only with very great difficulty using PL medium as the base because of strongly foaming fermentation products.

Column chromatography over Amberlite XAD-16 (1/10 of the starting volume) causes the troublesome detergents and some of the lipophilic and melanin-like compounds to be bound.

The aqueous eluate and the washing water are concentrated in a thin-layer evaporator at 60° C. and lyophilized.

Further purification of the rhizocticines is effected in accordance with Example 4.

EXAMPLE 6

Working-up from PL medium on a 5 l scale using Bio-Gel P2, Sephadex CM-25 and Sephadex G-10

5 l of culture broth are adjusted to a pH of 2.5 with 5N HCl. The resulting precipitate is separated off in a Sorvall centrifuge having a GSG 3 rotor at 10,000 g (approximately 8,000 rpm) and discarded. The supernatant (4.5 l) is then concentrated to dryness at 30° C.–40° C. and taken up in 500 ml of 70% ethanol.

Precipitation is carried out again at 4° C. and the precipitate is separated from the active supernatant. The precipitate is extracted twice with 200 ml of 70% ethanol each time and the active supernatants are combined and concentrated.

The active lyophilisate (27.5 g) is purified further by gel filtration over Bio-Gel P2 (200-400 mesh) using pure water as the eluant: v: 70 ml/h; gel bed: 875 mm ×50 mm; 10 ml/fraction. For this purpose, 9.1 g (above total amount divided into 3 aliquots), dissolved in 10-15 ml of deionized water, are introduced per Biogel run. The active fractions (fractions 98-124) are collected and lyophilized.

For the purpose of further purification the entire lyophilisate (1.85 g dissolved in 2 ml of 100 mM ammonium acetate) is introduced onto a Sephadex CM-25 column which has been equilibrated with 100 mM ammonium acetate in water (pH 5.5). The elution is likewise carried out with this starting buffer. v: 50 ml/h; 700 mm ×30 mm gel bed; 7 ml/fraction. The active fractions are combined and lyophilized three times in order substantially to remove the buffer (230 mg yield).

For the purpose of separation into rhizocticine A and B and simultaneously to effect fine purification, exclusion chromatography over Sephadex G-10 is carried out using 15% EtOH/85% $H_2O$ as the eluant: v: 16 ml/h; 4 ml/fraction; gel bed: 950 mm ×20 mm The entire antifungal activity is eluted in fractions 30-46.

Two activity maxima are produced:
rhizocticine B in fraction 33 rhizocticine A in fraction 41

The categorization was effected by means of TLC analysis (System I, ninhydrin detection). The pure fractions 30-34 (rhiz.B) are combined as are also the pure fractions 39-46 (rhiz.A) (rhiz.B 13 mg and rhiz.A 21 mg).

By means of high pressure liquid chromatography the uniformity of rhizocticine A and of rhizocticine B can then be tested and the mixture of fractions 35-38 separated into the pure components A and B.

Purity control for rhizocticine A and B

Column: RP18 Nucleosil, 5μ; 4.6×250 mm, preliminary
  column 4.6×10 mm
Mobile phase: 0.1% aqueous TFA (A)/ACN (B) 10 min. isocratic 100% A, then linear gradient of 0% B to 100% B in 30 min., flow 1 ml/min.

SEMI-PREPARATORY SEPARATION OF THE CONCENTRATE OF THE MIXED FRACTIONS

Column: RP18 Nucleosil, 5μ; 8×250 mm, preliminary column 8×40 mm
Mobile phase: 0.1% aqueous TFA; flow 3 ml/min.

Clarification of the structure of rhizocticine A and B was effected by customary methods, especially by amino acid analysis of the total hydrolysate; the clarification of the initially unknown amino acid L-APPA by means of $^{31}P$, $^{13}C$ and $^1H$ NMR; and the determination of the configuration by means of a comparison using gas chromatography of the hydrogenated hydrolysis mixture (TFA/trimethyl derivative) with DL-5-phosphonovaleric acid and sequence analysis by means of combined Dansyl-Edman degradation (Dansyl-AA, PTH-AA/TLC, GC), DNP derivatives and C-terminus determination by reduction with $B_2H_6$ to amino alcohols.

| Characterisation of rhizocticine A, B and L-APPA | | | |
|---|---|---|---|
| | rhiz. A | rhiz. B | L-APPA |
| nature | colourless powder | colourless powder | colourless powder |
| molecular formula | $C_{11}H_{22}N_5PO_6$ | $C_{16}H_{31}N_6PO_7$ | $C_5H_{10}NPO_5$ |
| molecular mass | 351 | 450 | 195 |
| sequence | L-Arg-L-APPA | L-Val-L-Arg-L-APPA | L-APPA |

Solubility: rhiz. A, B and APPA are readily soluble in water and 35% ethanol, moderately soluble in ethanol and higher alcohols, and insoluble in apolar solvents. Colour reaction: the compounds exhibit a positive ninhydrin reaction and chlorine/TDM reaction with 4,4'-tetramethyldiaminodiphenylmethane.

Thin-layer chromatographic characterization of rhizocticines A and B and of the hydrolytic cleavage product L-APPA:

Precoated silica gel plates 60 $F_{254}$ (Merck) are used for the thin-layer chromatography.

$R_F$ values are determined in freshly prepared eluant systems in saturated chambers lined with absorbent paper (manufacturer: Messrs. Camag/Muttenz, Switzerland). Customarily, 2 μl of an approximately 1% solution are applied. The run is 8-10 cm.

The eluants and the $R_F$ values are listed in the following Table.

| Eluant system (v/v) | |
|---|---|
| I) chloroform/methanol/12.5% ammonia | 2:2:1 |
| II) n-propanol/pyridine/glacial acetic acid/water | 15:10:3:12 |
| III) n-butanol/pyridine/glacial acetic acid/water | 15:12:3:10 |
| IV) n-propanol/water | 70:30 |
| V) n-butanol/glacial acetic acid/water | 2:1:1 |

| $R_F$ | rhiz. A | rhiz. B | APPA |
|---|---|---|---|
| I | 0.12 | 0.21 | 0.17 |
| II | 0.21 | 0.29 | 0.34 |
| III | 0.07 | 0.12 | 0.15 |
| IV | 0.02 | 0.04 | 0.21 |
| V | 0.10 | 0.12 | 0.16 |

The $^1H$-NMR spectrum and the $^{13}C$-NMR spectrum contain the following chemical shifts:

| $^1H$-NMR data of rhizocticine A (δ(ppm); $D_2O$) | | |
|---|---|---|
| measured values | literature values* | allocation |
| 4.05 | 4.13 | Arg α-H |
| 2.00 | 2.02 | Arg β-H (2H) |
| 1.80 | 1.88 | Arg γ-H |
| 3.29 | 3.27 | Arg δ-H |
| 4.93 (1H; d; J=8.9Hz) | 4.81 | APPA α-H |
| 5.71 (1H; m) | 5.64 | APPA β-H |
| 5.88 (1H; m) | 6.12 | APPA γ-H |
| 2.62 (2H; m; J=9.3Hz) | 2.72 | APPA δ-H |

| $^{13}C$-NMR data of rhizocticine A (δ(ppm); $D_2O$) | | | |
|---|---|---|---|
| measured values | literature values* | multiplicities** | |
| 179.8 | 175.2 | Arg | (C=O) |
| 55.3 | 55.1 | Arg | (CH) |
| 30.4 | 28.5 | Arg | ($CH_2$) C-3 |
| 25.8 | 24.9 | Arg | ($CH_2$) C-4 |
| 42.9 | 41.5 | Arg | ($CH_2$) C-5 |
| 159.3 | 157.5 | Arg | (C=NH) |
| 171.1 | 172.7 | APPA | (C=O) |
| 55.7 (s) | 51.5 | APPA | (CH) |
| 128.6 (d; J=13Hz) | 123.5 | APPA | (CH) |
| 131.4 (d; J=10Hz) | 132.9 | APPA | (CH) |
| 31.6 (d; J=128Hz) | 29.3 | APPA | ($CH_2$) |

| $^{13}C$-NMR data of rhizocticine B (δ(ppm); $D_2O$) | | |
|---|---|---|
| 179.8 | Arg | C-1 |
| 174.3 | APPA | C-1 |
| 172.2 | Val | C-1 |
| 159.5 | Arg | C-6 |
| 130.7 | APPA | C-4 (doublet 9.5Hz) |
| 129.4 | APPA | C-3 (doublet 13.2Hz) |
| 61.3 | Val | C-2 |
| 56.2 | Arg | C-2 |
| 55.9 | APPA | C-2 |
| 43.2 | Arg | C-5 |
| 31.5 | APPA | C-5 (doublet 127Hz) |
| 32.8 | Arg | C-3 |
| 30.8 | Val | C-3 |
| 26.9 | Arg | C-4 |
| 20.5 | Val | C-4 |
| 19.5 | Val | C-4' |

*B. K. Park, A. Hirota, H. Sakai, Agric. Biol. Chem. 41, 573-579 (1977)
**from the spin-echo experiment

EXAMPLE 7

Isolation of rhizocticine C and D

After Sephadex G-10 purification isolates of rhizocticine B are microheterogeneous, that is to say 0.5%-5% of the N-terminal amino acid valine is replaced by leucine and by isoleucine. Small amounts of the likewise antifungal tripeptides rhizocticine C (L-Ile-L-Arg-L-APPA) and rhizocticine D (L-Leu-L-Arg-L-APPA) can be isolated from the mixture by means of HPLC.

Column: RP18 Nucleosil, 5μ; 4.6×250 mm, preliminary column 4.6×10 mm

Mobile phase: 0.01 M $KH_2PO_4$, isocratic; flow 1 ml/min.

Categorization and identification are effected by means of gas-chromatographic AA determination. $R_F$ values (TLC system II):
rhizocticine C $R_F=0.31$
zocticine D $R_F=0.28$

EXAMPLE 8

Preparation of L-2-amino-5-phosphono-3-cis-pentenoic acid (L-APPA) from the rhizocticines by hydrolysis 7 mg of rhizocticine A are hydrolyzed in 1 ml of 6N HCl for 18 hours at 110° C. and blown to dryness in a stream of nitrogen.

The concentrate is taken up in 200 µl of water and for the purpose of subsequent purification (removing arginine) is introduced onto a Dowex 50 WX8 ion-exchanger column ($H^+$ form, 50–100 mesh, 65×8 mm). While arginine is bound, L-APPA can be eluted simply with deionized water (pH 6). The fractions that are uniform according to thin-layer chromatography (TLC monitoring over silica gel, yellow coloration with ninhydrin, $R_F=0.16$ in system V) are combined and lyophilized. 3.1 mg of colorless L-APPA are obtained.

In analogous manner the rhizocticines B, C and D can be cleaved and L-APPA obtained from the cleavage products.

$^1$H-NMR data for L-APPA from the HPLC separation of the hydrolysate of rhizocticine A (δ(ppm); $D_2O$; 400.13 MHz)

| measured values | literature values* | chem. shift |
|---|---|---|
| 2.68 (2H; m; m; J=7.5Hz) | 2.72 (2H; d; d; J=8.4Hz) | δCH |
| 4.59 (1H; d; J=9.8Hz) | 4.81 (1H; d; J=9.5Hz) | αCH |
| 5.63 (1H; m) | 5.64 (1H; d/t; J=5.2, 9.5Hz) | βCH |
| 6.04 (1H; m) | 6.12 (1H; m) | γCH |

$^{13}$C-NMR data for L-APPA from the HPLC separation of the hydrolysate of rhizocticine A (δ(ppm); $D_2O$; 100.6 MHz)

| measured values | literature values* | |
|---|---|---|
| 176.19 (s) | 172.7 (s) | C-1 |
| 54.03 (s) | 51.5 (s) | C-2 |
| 126.48 (d; J=13Hz) | 123.5 (d; J=12Hz) | C-3 |
| 134.15 (d; J=10Hz) | 132.9 (d; J=11Hz) | C-4 |
| 31.23 (d; J=127Hz) | 29.3 (d; J=127Hz) | C-5 |

*B. K. Park, A. Hirota, H. Sakai, Agric. Biol. Chem. 41, 573–579 (1977)

The determination of the configuration is effected indirectly by means of a comparison using gas chromatography of the hydrogenated hydrolysis mixture containing the L-5-phosphonovaleric acid with D,L-5-phosphonovaleric acid. Conditions of the gas chromatography: Chirasil-Val, temperature program 5 min. at 80° C. isotherm, then 3°/min. to 220° C.; carrier gas $H_2$ (0.7 bar); (TFA/trimethylsilyl) derivatives.

EXAMPLE 9

Preparation of L-2-amino-5-phosphono-3-cis-pentenoic acid (L-APPA) from the rhizocticines by reaction with thermolysin 200 µl of thermolysin (2 mg/ml) are added to 7 mg of rhizocticine A in 1.5 ml of 0.05N N-ethylmorpholinium acetate, 0.01 M $CaCl_2 \times 6H_2O$ (pH 7.8). At T =41° C. the hydrolysis is complete after 30 hours (ion-exchanger/amino acid analysis). The enzyme is deactivated by the addition of dilute HCl to a pH of 3, the solution is concentrated by evaporation in vacuo in a rotary evaporator, and the residue is taken up in a little 0.05 N acetic acid and introduced onto a Sephadex G-25 column (10×250 mm, eluant 0.05N acetic acid). The APPA fractions, which can be colored yellow on the TLC plate using ninhydrin (system V), are collected and concentrated by evaporation.

The concentrate is worked up as described in Example 8. 3.1 mg of colorless L-APPA are obtained.

In analogous manner L-APPA can be obtained from the rhizocticines by reaction with carboxypeptidase A and trypsin. Depending on the reaction conditions, 3–5 days' incubation is required for quantitative hydrolysis.

Reaction conditions for reactions with enzymes:
enzyme/substrate ratio 5%–10%
incubation temperature T=37° C.; for reaction with carboxypeptidase A: T=29° C.
buffer: 0.05 N N-ethylmorpholinium acetate, 0.01 M $CaCl_2 \times 6H_2O$, pH 7.8
substrate concentration: 0.5 mg/ml The enzyme reaction is monitored at suitable time intervals, by removing aliquots (10 µl) from the reaction solution each time and acidifying to a pH of 2.5 with 1N HCl in order to end the reaction.

The samples are passed on to an automated ion-exchanger/amino acid analysis for analysis.

EXAMPLE 10

Enzymatic conversion of rhizocticine B into A

The enzymatic hydrolysis of rhizocticine B (L-Val-L-Arg-L-APPA) to rhizocticine A with removal of valine is effected with pronase from Streptomyces griseus, a peptidase of low specificity. The enzymatic degradation of L-Val-L-Arg-L-APPA is effected quantitatively within a few minutes (approximately 15 minutes), the antifungal activity being obtained. By removing the N-terminal amino acid valine, rhizocticine A is formed. The hydrolysis is confirmed by thin-layer chromatography and ion-exchanger/amino acid analysis.

After 12 hours there is still no loss of activity to be found in the antibiotically active dipeptide formed.

Native rhizocticine A also remains inert during the pronase treatment.

The separation of the cleavage products of rhizocticine after the pronase treatment is effected on the amino acid analyzer or by the methods described hereinbefore.

EXAMPLE 11

Preparation of rhizocticine A (L-Arg-L-APPA) starting from L-APPA

51 µmol (6.9 mg) of HOBt dissolved in 250 µl of DMF are added to 51 µmol (16 mg) of Boc-L-Arg-OH x HCl ×$H_2O$. While stirring, 10.7 mg of DCC are added, the whole is stirred for 30 minutes at room temperature and the insoluble DCU is filtered off. The filtrate is added to 40 µmol (8 mg) of L-APPA dissolved in 200 µl of DMF and after the addition of 2 equivalents (4 µl) of N-ethylmorpholine the whole is stirred for 4 hours at room temperature. The solvent is evaporated off under a high vacuum in a rotary evaporator. The residue is digested with 2 ml of water and filtered off. The filtrate is adjusted to pH 7, introduced onto a Dowex 1×4 column (OH form, 7×50 mm) and washed with water and then with 0.1 N acetic acid, and the synthesis product is eluted with 2N acetic acid. The fractions are concentrated by evaporation in a rotary evaporator and lyophilized Boc-L-Arg-L-APPA is obtained; $R_F=0.28$ (silica gel, n-propanol/-pyridine/glacial acetic acid/water 15:10:3:12).

11 μmol (5 mg) of Boc-L-Arg-L-APPA are stirred with 1 ml of TFA/dichloromethane 1:1 for 15 minutes at room temperature. Evaporation is then carried out under a high vacuum in a rotary evaporator, 3 ml of dichloromethane are added and evaporation is again carried out. The residue is taken up in 0.01 N HCl and lyophilized. The title compound L-Arg-L-APPA is obtained (in the form of the hydrochloride); $R_F=0.21$ (silica gel, N-propanol/pyridine/glacial acetic acid/water 15:10:3:12).

EXAMPLE 12

Preparation of rhizocticine B (L-Val-L-Arg-L-APPA) starting from L-Arg-L-APPA

20 μmol (6.2 mg) of Boc-L-Val-OSu are dissolved in 1 ml of DMF, then 40 μmol (4 μl) of N-ethylmorpholine and 13 μmol (5 mg) of L-Arg-L-APPA ×HCl are added and the whole is stirred for 16 hours at room temperature. The reaction mixture is subjected to evaporation under a high vacuum in a rotary evaporator, the residue is taken up in 2 ml of water and the whole is extracted three times with 2 ml of ethyl acetate each time.

The aqueous phase is concentrated to dryness, taken up in 0.01N HCl and lyophilized. Boc-L-Val-L-Arg-L-APPA is obtained; $R_F=0.23$ (silica gel, n-butanol/glacial acetic acid/water 2:1:1).

9 μmol (5 mg) of Boc-L-Val-L-Arg-L-APPA are stirred with 1 ml of TFA/dichloromethane 1:1 for 30 minutes at room temperature. The reaction mixture is subjected to evaporation under a high vacuum in a rotary evaporator. The residue is taken up in 200 μl of DMF. After the addition of ethereal HCl (2 ml) the colorless product precipitates. The title compound L-Val-L Arg-L-APPA is obtained (in the form of the hydrochloride); $R_F=0.12$ (silica gel, n-butanol/glacial acetic acid/water 2:1:1).

EXAMPLE 13

The following tripeptides, or their hydrochlorides, can be prepared analogously to Examples 11 and 12:

L-Ile-L-Arg-L-APPA
L-Leu-L-Arg-L-APPA
L-Ala-L-Arg-L-APPA
L-HomoArg-L-APPA
L-Val-L-HomoArg-L-APPA
L-Ile-L-HomoArg-L-APPA
L-Leu-L-HomoArg-L-APPA

EXAMPLE 14

Preparation of L-Val-L-Lys-L-APPA starting from L-APPA

A solution of 40 μmol (18.7 mg) of Fmoc-L-Lys(-Boc)-OH, 40 μmol (5.4 mg) of HOBt and 8.3 mg of DCC in 1 ml of DMF is stirred for 30 minutes at room temperature, filtered and the filtrate is added to 40 μmol (8 mg) of L-APPA dissolved in 0.5 ml of DMF. After stirring for 4 hours at room temperature, evaporation is carried out under a high vacuum in a rotary evaporator, the residue is taken up in 250 μl of DMF, the insoluble material is filtered off and the filtrate is introduced onto a Sephadex LH2O column (200×8 mm, eluant DMF). The chromatographically uniform fractions (TLC monitoring on silica gel in chloroform/methanol/water 65:25:4 $R_F=0.19$) are concentrated by evaporation, taken up in 5 ml of t-butanol and lyophilized.

A solution of 18 μmol (12 mg) of Fmoc-L-Lys(Boc)-L-APPA-OH in 2 ml of 10% piperidine in DMF is stirred for 30 minutes at room temperature and evaporated under a high vacuum in a rotary evaporator. The residue is taken up in 0.5 ml of DMF, and 4 ml of diethyl ether and 4 ml. of petroleum ether (30°-50°) are added. At 4° C. the colorless L-Lys(Boc)-L-APPA precipitates out; $R_F=0.25$ (silica gel, chloroform/methanol/12.5% ammonia 2:2:1).

19 μmol (2 μl) of N-ethylmorpholine are added to a solution of 12 μmol (5 mg) of L-Lys(Boc)-L-APPA and 20 μmol (6.3 mg) of Boc-L-Val-OSu in 1 ml of DMF and the whole is stirred for 12 hours at room temperature. The reaction mixture is subjected to evaporation under a high vacuum in a rotary evaporator, the residue is digested with 2 ml of water and extracted three times with 2 ml of ethyl acetate each time, and the aqueous phase is lyophilized.

1 ml of TFA is added to 10 μmol (6.2 mg) of Boc-L-Val-L-Lys(Boc)-L-APPA and after 30 minutes evaporation is carried out under a high vacuum in a rotary evaporator, the residue is taken up in 1 ml of DMF and the whole is precipitated with 3 ml of diethyl ether. The precipitate is taken up in 0.01 N HCl and lyophilized. L-Val-L-Lys-L-APPA is obtained (in the form of the hydrochloride); $R_F=0.34$ (silica gel, n-propanol/pyridine/glacial acetic acid/water 15:10:3:12).

The following tripeptides, or their hydrochlorides, can be prepared in the same manner:
L-Ile-L-Lys-L-APP
L-Leu-L-Lys-L-APP
L-Ala-L-Lys-L-APP
L-Val-L-Orn-L-APPA
L-Ile-L-Orn-L-APPA
L-Leu-L-Orn-L-APPA
L-Ala-L-Orn-L-APPA

EXAMPLE 15

Preparation of L-Lys-L-APPA

153 μmol (17 μl) of N-ethylmorpholine are added to a solution of 40 μmol (8 mg) of L-APPA and 70 μmol (29.8 mg) of Boc-L-Lys(Boc)-OSu in 2 ml of DMF and the whole is stirred for 12 hours at room temperature. The reaction mixture is subjected to evaporation under a high vacuum in a rotary evaporator and the residue is taken up in 0.5 ml of DMF and introduced onto a Sephadex LH2O column (200×10 m, eluant DMF). The chromatographically uniform fractions (TLC monitoring on silica gel in n-butanol/glacial acetic acid/water 2:1:1; $R_F=0.43$) are combined, concentrated by evaporation, taken up in t-butanol and lyophilized.

A mixture of 9.6 μmol (5 mg) of Boc-L-Lys(Boc)-L-APPA and 0.5 ml of TFA is stirred for 30 minutes at room temperature, concentrated by evaporation in a rotary evaporator, taken up in 0.01 N HCl and lyophilized. L-Lys-L-APPA is obtained (in the form of the hydrochloride); $R_F=0.15$ (silica gel, n-butanol/glacial acetic acid/water 2:1:1).

L-Orn-L-APPA, or its hydrochloride, can be prepared in the same way.

EXAMPLE 16

Freeze-dried ampoules or vials containing 0.5 g of rhizocticine A as active ingredient can be prepared in the following manner:

| Composition: (for 1 ampoule or vial) | |
| --- | --- |
| active ingredient | 0.5 g |
| mannitol | 0.05 g |

A sterile aqueous solution consisting of active ingredient and mannitol is introduced under aseptic conditions into 5 ml ampoules or 5 ml vials, which are then sealed and checked.

Δ-Δ activity against *Paecilomyces variotii* Tü 137 (mm inhibiting areola diameter)
O - O activity against *Saccharomyces cerevisiae* Tü 125 (mm inhibiting areola diameter),
♦ - ♦ sediment (%), ● - ● pH,
■ - ■ pO$_2$ (%).

Figure 1:
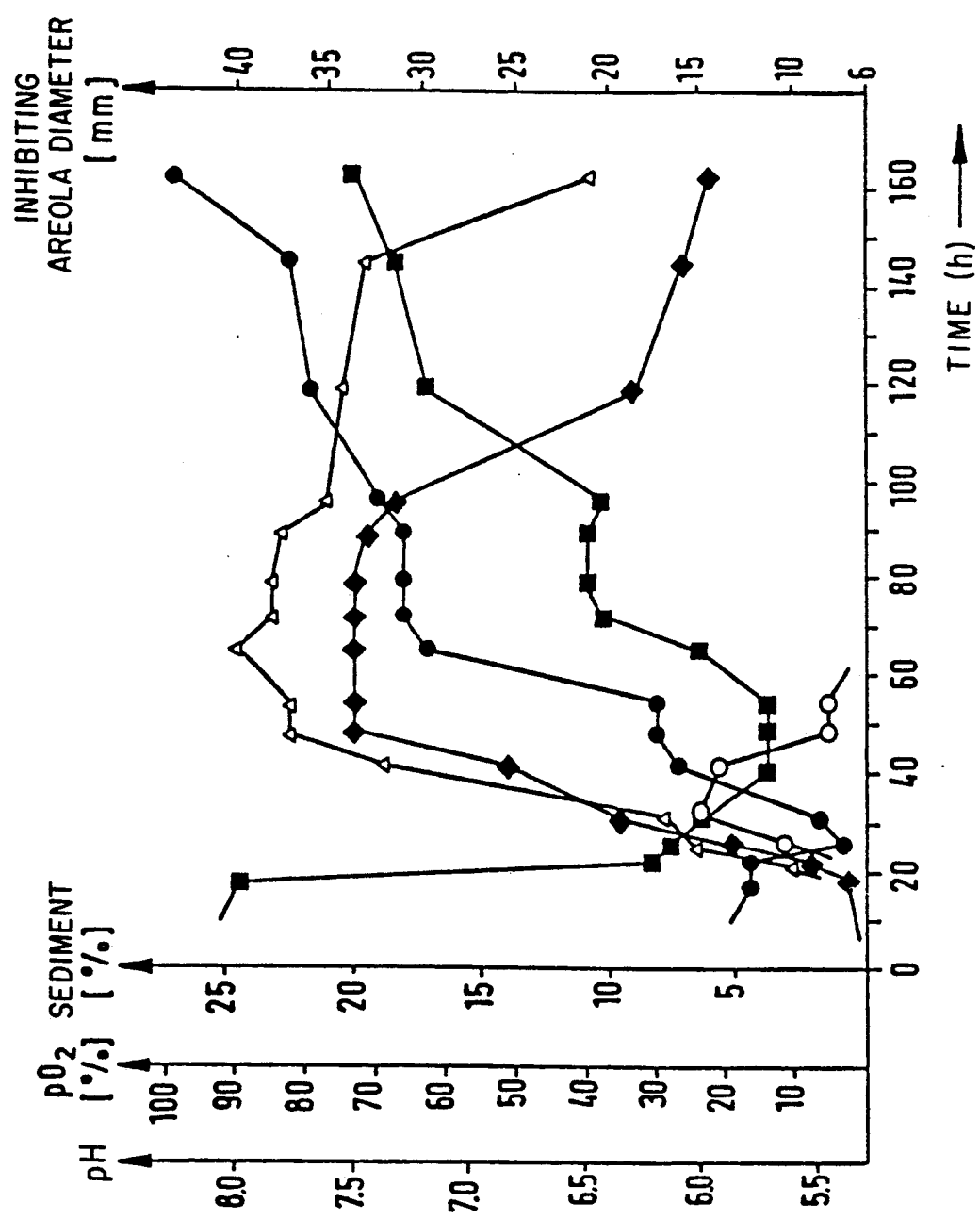
FIG. 1: Fermentation of *Bacillus subtilis* ATCC 6633 on a 20 l scale (PL medium, 27° C.)
Figure 2:
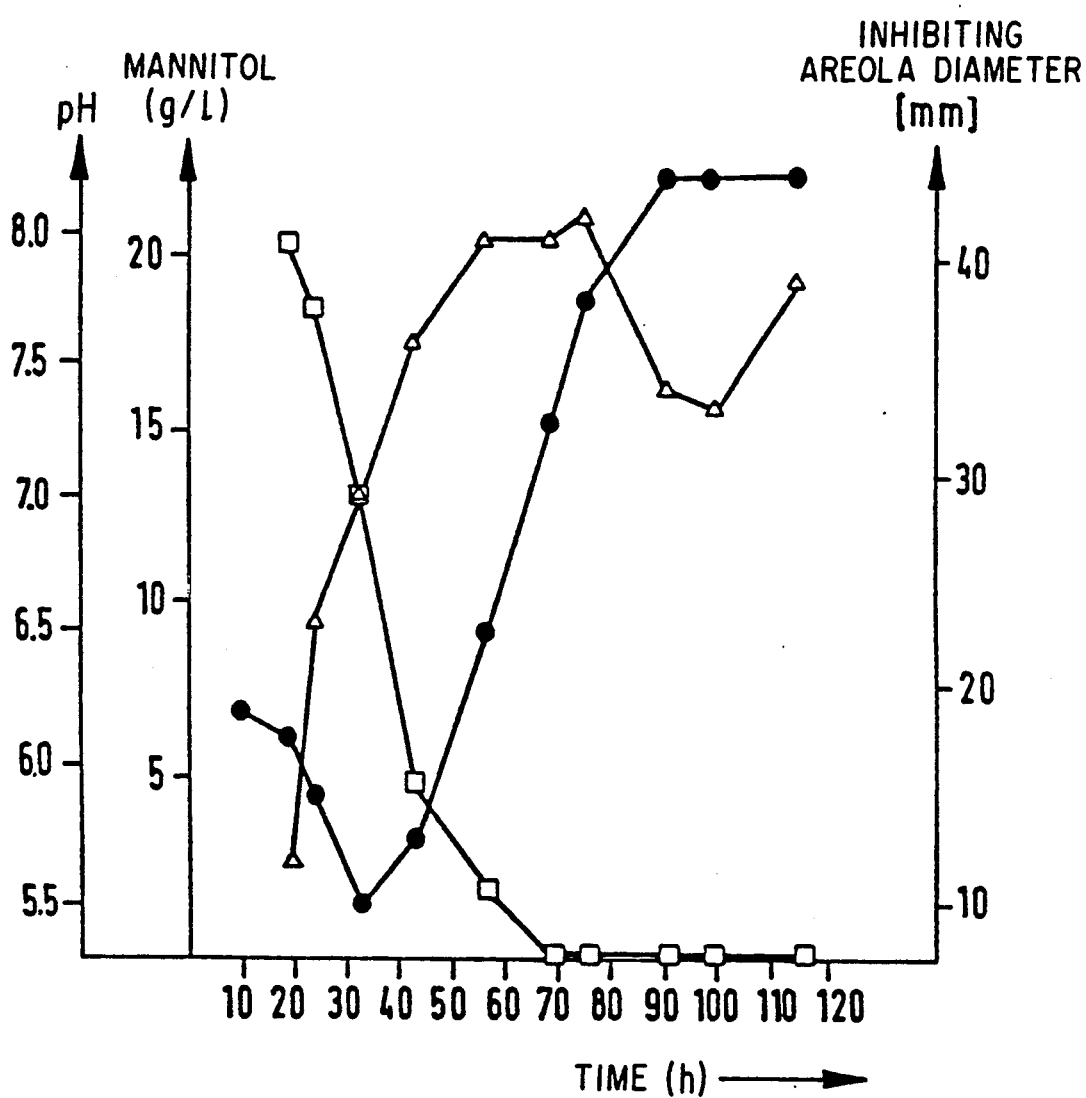

FIG. 2: Fermentation of *Bacillus subtilis* ATCC 6633 on a 200 l scale (PL medium, 27° C.)

Δ-Δ activity against *Paecilomyces variotii* Tü 137 (mm inhibiting areola diameter),
● - ● pH, □ - □ mannitol content (g/l).

We claim:
1. Optically pure L-2-amino-5-phosphono-3-cis-pentenoic acid (L-APPA), or a salt thereof.

* * * * *